United States Patent [19]

Kupperman et al.

[11] Patent Number: 4,559,827
[45] Date of Patent: Dec. 24, 1985

[54] ULTRASONIC SHEAR WAVE COUPLANT

[75] Inventors: David S. Kupperman, Oak Park; Ronald N. Lanham, Lockport, both of Ill.

[73] Assignee: The United States of America as represented by the United States Department of Energy, Washington, D.C.

[21] Appl. No.: 599,108

[22] Filed: Apr. 11, 1984

[51] Int. Cl.⁴ ............................................ G01N 29/04
[52] U.S. Cl. ...................................................... 73/644
[58] Field of Search .......................... 73/644; 310/336

[56] References Cited

U.S. PATENT DOCUMENTS

| 3,663,842 | 5/1972 | Miller | 73/644 |
| 3,678,737 | 7/1972 | Miller | 73/644 |
| 3,714,816 | 2/1973 | Miller | 73/644 |
| 3,732,444 | 5/1973 | Miller | 73/644 |
| 3,763,694 | 10/1973 | Rathburn et al. | 73/644 |
| 4,069,083 | 1/1978 | Palmer | 73/644 |

Primary Examiner—Anthony V. Ciarlante
Attorney, Agent, or Firm—William Lohff; James W. Weinberger; Judson R. Hightower

[57] ABSTRACT

Ultrasonically testing of an article at high temperatures is accomplished by the use of a compact layer of a dry ceramic powder as a couplant in a method which involves providing an ultrasonic transducer as a probe capable of transmitting shear waves, coupling the probe to the article through a thin compact layer of a dry ceramic powder, propagating a shear wave from the probe through the ceramic powder and into the article to develop echo signals, and analyzing the echo signals to determine at least one physical characteristic of the article.

7 Claims, 2 Drawing Figures

ULTRASONIC SHEAR WAVE COUPLANT

CONTRACTUAL ORIGIN OF THE INVENTION

The United States Government has rights in this invention pursuant to Contract No. W-31-109-ENG-38 between the U.S. Department of Energy and the University of Chicago representing Argonne National Laboratory.

BACKGROUND OF THE INVENTION

This invention relates to the ultrasonic testing of ceramic, metallic and other articles such as pipe, plates and the like using shear waves and more particularly to ultrasonic testing at high temperatures of about 300°–1000° C.

Conventional ultrasonic testing is based on longitudinal waves and mode converted shear waves. Testing by the use of normal incidence shear waves is particularly useful for measurements of thickness and certain physical characteristics such as shear modulus with good accuracy. In general, the velocity of the shear wave is less than that of the longitudinal wave and therefore provides a greater resolution and an improved accuracy. These tests are usually carried out at frequencies in the order of about 1–10 MHz and often about 2–5 MHz.

Previously, ultrasonic testing with shear waves have been carried out at low temperatures using a variety of couplants such as a wedge of plastic (for mode converting longitudinal waves to shear waves), viscous liquids, and adhesives such as epoxy.

Other couplants for ultrasonic testing include adhesives coated with or containing minute glass beads as disclosed in U.S. Pat. Nos. 3,678,737, 3,714,816 and 3,732,444; and certain polymeric materials such as silicones, polyurethanes and polyesters as disclosed in U.S. 3,663,842 and U.S. Pat. No. 3,763,694. These couplants appear to be directed to the use of longitudinal waves.

In particular with regard to couplants for ultrasonic testing by shear waves, the above couplants when used for nonpermanent attachment of the probe do not perform satisfactorily when the article is at temperatures in the order of 300°–1000° C. In general, the materials have limited stability (physically and/or chemically) at the higher temperatures. In addition, as the test conditions are changed between high and low temperatures, some solid couplants tend to break apart.

Accordingly, one object of the invention is a high temperature couplant for coupling a shear-wave transmitting probe to an article. Another object is a high temperature couplant which remains useful after being subjected to significant temperature variations. A further object is a technique for the ultrasonic testing of articles at high temperatures. These and other objects will become apparent from the following detailed description.

SUMMARY OF THE INVENTION

Briefly, the invention involves a method for ultrasonically testing of an article by providing an ultrasonic transducer as a probe capable of transmitting shear waves, coupling the probe to the article through a thin compact layer of a dry ceramic powder, propagating a shear wave from the probe through the ceramic powder and into the article to develop echo signals, and analyzing the echo signals to determine at least one physical characteristic of the article. The ceramic powders of particular importance include yttrium chromite and magnesium oxide. Advantageously, they are composed of particles sized in the range of about 0.3–3.0 microns and preferably in the range of 0.3–1.0 microns. Tests with powders of alumina, silicon nitride and silicon carbide have provided less than favorable results.

DETAILED DESCRIPTION OF THE PREFERRED EMBODIMENT

Figure 1:
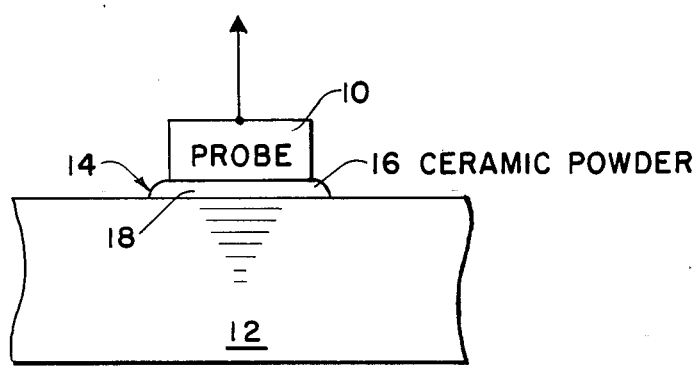
FIG. 1 is a side view of one embodiment of the invention.

As illustrated in FIG. 1, an ultrasonic transducer 10 (a standard normal incidence shear probe) is placed in close proximity to article 12 which may represent a wall section (approximately 0.5–1.0 inch in thickness) of a metal pipe (aluminum) or ceramic plate. As a high temperature couplant, a thin compact layer 14 of a dry ceramic powder 16 is provided between the transducer 10 and article 12 and in contact with each and thereby couples the probe to the article. The surface 18 of article 12 is clean and milled smooth. Transducer 10 is capable of generating a shear wave in the range of about 1–10 MHz and of withstanding temperatures above about 300° C.

Layer 14 is approximately 15–50 microns in thickness and formed of a compacted ceramic powder with particles in the range of about 0.3–3.0 microns and preferably about 0.3–1.0 micron. The ceramic advantageously has a modulus of elasticity below that for silicon carbide, and preferably below by at least 25%. Preferably, the ceramic is yttrium chromite, magnesium oxide or mixtures of these materials.

Under the usual high temperature conditions, the article is first heated to above about 300° C. and the test carried out by generating an ultrasonic shear wave in the transducer 10 through couplant 16 into article 12. The echo signals in the article are then analyzed in the conventional manner and displayed on a scope.

Figure 2:
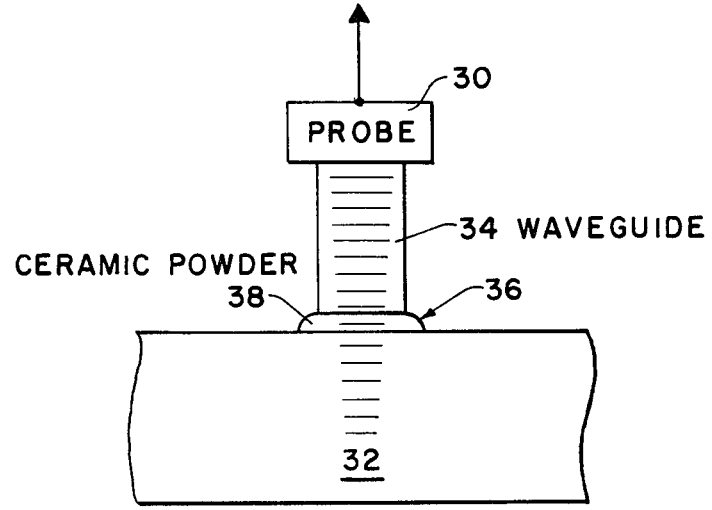
FIG. 2 is a side view of a second embodiment of the invention.

In FIG. 2, an ultrasonic transducer 30 is protected from higher temperatures in the article 32 by a waveguide 34 which acts as a buffer and is illustrated as a steel member about 5–6 inches long. A thin compact layer 36 of ceramic powder 38 acts to couple the transducer 30, buffer 34 and article 32.

The foregoing description of embodiments of the invention has been presented for purposes of illustration and description. It is not intended to be exhaustive or to limit the invention to the precise form disclosed, and obviously many modifications and variations are possible in light of the above teaching.

The embodiments of the invention in which an exclusive property or privilege is claimed are defined as follows:

1. A method of ultrasonically testing a metallic or ceramic article at temperatures in the order of about 300°–1000° C. comprising the steps of
    providing an ultrasonic transducer capable of generating a shear wave,
    ultrasonically coupling the ultrasonic transducer to a surface of the article through a thin compact layer of a dry ceramic powder, the ceramic powder having a modulus of elasticity about 25% below that for silicon carbide, propagating a shear wave from the transducer through the ceramic powder and into the article to develop echo signals, and analyzing the echo signals to determine at least one physical characteristic of the article.

2. The method of claim 1 wherein the ultrasonic coupling is carried out with a ceramic powder composed of particles sized in the range of 0.3–3.0 microns.

3. The method of claim 2 wherein the ultrasonic coupling is carried out with a ceramic selected from the group consisting of yttrium chromite and magnesium oxide.

4. The method of claim 3 including the step of providing a buffer member between the ultrasonic transducer and thin layer to protect the probe from excessive temperatures.

5. The method of claim 4 wherein the layer is heated to a temperature in the range of about 300°–1000° C.

6. The method of claim 5 wherein the ceramic is yttrium chromite.

7. The method of claim 5 wherein the ceramic is magnesium oxide.

* * * * *